United States Patent [19]

Buske et al.

[11] 4,451,408

[45] May 29, 1984

[54] PROCESS OF PREPARING SULFONIUM ORGANOSULFONATES

[75] Inventors: Gary R. Buske; Richard G. Pews, both of Midland, Mich.

[73] Assignee: The Dow Chemical Company, Midland, Mich.

[21] Appl. No.: 453,312

[22] Filed: Dec. 27, 1982

Related U.S. Application Data

[62] Division of Ser. No. 346,691, Feb. 8, 1982.

[51] Int. Cl.³ .................. C07C 143/02; C07C 143/26; C07C 143/28
[52] U.S. Cl. ........................... 260/505 R; 260/513 R
[58] Field of Search .............. 568/18, 36; 260/513 R, 260/505 R

[56] References Cited

U.S. PATENT DOCUMENTS 2,774,793 12/1956 DeJong et al. ...................... 568/18

OTHER PUBLICATIONS

S. Smiles, J. Chem. Soc., 696–708 (1906).
S. Smiles, J. Chem. Soc., 745–762 (1908).
J. V. Crivello, et al., J. Poly. Sci., Poly. Chem. Ed., 17, 977–999 (1979).
J. V. Crivello, et al., J. Poly. Sci., Poly. Chem. Ed., 18, 2677–2695 (1980).
J. V. Crivello, et al., J. Poly. Sci., Poly. Chem. Ed., 18, 2697–2714 (1980).

*Primary Examiner*—Nicky Chan
*Attorney, Agent, or Firm*—Douglas N. Deline

[57] ABSTRACT

Monomeric and polymeric triarylsulfonium complex salts which may be prepared by contacting diarylsulfoxides or polymeric arylsulfoxides with aromatic compounds in the presence of an organosulfonic acid are described. An example is tris-(4-phenoxyphenyl)sulfonium methane sulfonate prepared by reaction of bis-(4-phenoxyphenyl)sulfoxide, diphenyl ether and methane sulfonic acid. The compounds demonstrate useful corrosion inhibiting properties.

15 Claims, No Drawings

PROCESS OF PREPARING SULFONIUM ORGANOSULFONATES

CROSS-REFERENCE TO RELATED APPLICATION

This is a divisional, of application Ser. No. 346,691, filed Feb. 8, 1982.

BACKGROUND OF THE INVENTION

This invention relates to triarylsulfonium complex salts. More particularly, the invention relates to triarylsulfonium organosulfonates and anion-exchanged derivatives thereof that have useful properties either with or without modification for use as corrosion inhibitors, phase-transfer catalysts, catalysts for hydrocarbon oxidation, flame-retardant additives, biological agents such as herbicides and animal growth promoters, flocculants in waste water treatment and mineral ore processing and refining, and as complex salt photoinitiators. The invention further relates to a novel process for preparing the triarylsulfonium organosulfonates of the invention.

In U.S. Pat. No. 2,807,648, a process is described for the preparation of triarylsulfonium chlorides by the reaction of an aryl hydrocarbon, aluminum chloride, sulfur monochloride and chlorine. The process has proven difficult for commercial use due to the hazardous reactants involved. Furthermore, it has recently been discovered that the process does not prepare highly pure triarylsulfonium salts as had been previously thought. For example, in U.S. Pat. No. 4,173,476 at column 6, line 36 et seq. it is disclosed that the reaction mixture formed according to this process contains up to about 55 percent of diphenyl(4-(phenylthio)phenyl)sulfonium chloride with only minor amounts of the expected triphenylsulfonium chloride.

S. Smiles in *J. Chem. Soc.*, 696–708 (1906) at page 701, described a process for preparing triarylsulfonium sulfates by heating, e.g., di(p-ethoxyphenyl)sulfoxide with ethoxybenzene in the presence of sulfuric acid. The process disadvantageously introduced quantities of sulfonated benzene derivatives. Also disclosed by the same reference was a process for preparing triarylsulfonium phosphate salts by reacting diphenyl sulfoxide with ethoxybenzene in the presence of phosphoric acid.

The above-identified U.S. Pat. No. 4,173,476 describes a further process wherein triphenylsulfonium phosphates were prepared by reacting diphenyl sulfoxide with diphenyl sulfide in the presence of phosphorus pentoxide.

It would be desirable to prepare triarylsulfonium salts without disadvantageously contaminating the desired product with derivatives formed by interaction of the catalyst and the reactants.

It would be further desirable to provide a process for preparation of triarylsulfonium salts that may suitably employ non-activated and relatively unreactive aromatic compounds in place of reactive aromatic compounds such as alkoxybenzenes, or diphenyl sulfide employed in the prior art.

Finally, it would be desirable to prepare novel triarylsulfonium salts of high purity having desirable properties for use in numerous industrial applications.

SUMMARY OF THE INVENTION

According to the invention an improved process is provided for preparation of monomeric and polymeric triarylsulfonium complex salts comprising compounds corresponding to the formula:

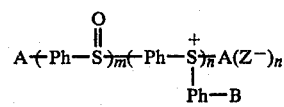

wherein
Ph is phenylene, diphenylene or oxydiphenylene;
A and B independently each occurrence are hydrogen, $C_{1-4}$ alkyl, phenyl, alkoxy or phenoxy;
m is an integer greater than or equal to zero, equal to the number of sulfoxide moieties in the complex salt;
Z is a counterion selected from the group consisting of $RSO_3^-$, $BF_4^-$, $PF_6^-$, $AsF_6^-$ and $SbF_6^-$, where R is lower alkyl, phenyl or tolyl; and
n is an integer greater than or equal to one, equal to the number of sulfonium moieties in the complex salts.

The process comprises contacting a diarylsulfoxide or polymeric arylsulfoxide corresponding to the formula:

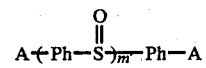

with an aromatic compound of the formula B—Ph—H in the presence of an organosulfonic acid of the formula R—$SO_3$H at elevated temperatures,
wherein A, Ph, B and R are as previously defined; and
m' is an integer greater than or equal to one, equal to the number of sulfoxide moieties in the compound.

The organosulfonate counterions may be exchanged for the other counterions specified by contacting the triarylsulfonium complex salts with alkali metal salts of the desired counterion.

Further included in the invention are the novel monomeric and polymeric triarylsulfonium complex salts formed by the process.

DETAILED DESCRIPTION OF THE INVENTION

The diarylsulfoxides and polymeric arylsulfoxides employed in the invention are either known compounds or they may be prepared according to known techniques. Suitable monomeric compounds include diphenyl sulfoxides, $C_{1-4}$ alkyl-, $C_{1-4}$ alkoxy- or phenoxy-substituted diphenyl sulfoxides, di(biphenyl)sulfoxides, and $C_{1-4}$ alkyl-, $C_{1-4}$ alkoxy- or phenoxy-substituted di(biphenyl)sulfoxides.

Preferred monomeric diarylsulfoxides are diphenyl sulfoxides ring-substituted in the para positions with the above groups. A preferred reactant is bis(4-phenoxyphenyl)sulfoxide which produces (4-phenoxyphenyl)-substituted sulfonium compounds having improved corrosion-inhibiting properties.

Polymeric arylsulfoxides are easily prepared, for example, by the Lewis acid catalyzed reaction of the previously identified aromatic compounds, B—Ph—H, with thionyl chloride. A preferred aromatic compound is diphenyl ether, thereby producing polymeric arylsulfoxides of the formula:

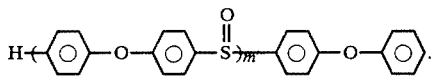

Suitably, m' in such polymeric arylsulfoxides is from 2 to about 30, preferably from about 2 to about 10.

The aromatic compounds which are reacted with the above diarylsulfoxides and polymeric arylsulfoxides include benzene, monosubstituted $C_{1-4}$ alkyl- or $C_{1-4}$ alkoxybenzenes, phenylbenzene and diphenyl ether. Preferred are aromatic compounds capable of entering into Friedel-Crafts reactions. Preferred aromatic compounds are toluene, methoxybenzene and diphenyl ether. A most preferred aromatic compound is diphenyl ether.

The organosulfonic acids for use according to the invention include methane sulfonic acid and other alkyl sulfonic acids, as well as benzene sulfonic acid and toluene sulfonic acid. Methane sulfonic acid is preferred.

The previously identified reactants are combined in a reaction vessel and heated to elevated temperatures. Suitable temperatures are from about 70° C. to about 150° C., preferably from 80° C. to about 110° C. The time for the reaction is dependent on the reaction conditions employed and the degree of completion desired for the reaction. Generally, the reaction is completed within about 24 hours.

The reactants may be combined in any order. An excess of organosulfonic acid is employed. Suitably from about 5 to 10 equivalents of acid are employed per equivalent of sulfoxide reactant. The aromatic reactant may also be present in an excess over that required for the reaction. Suitably, amounts of aromatic compound from 1 equivalent to about 10 equivalents per equivalent of sulfoxide reactant are employed.

A reaction solvent may be employed as an aid in mixing and contacting the reactants. Suitable solvents include inert organic liquids such as halogenated aliphatics, e.g., methylene chloride, ethylene chloride, etc.

It is recognized, particularly for the polymeric complex sulfonium salts of the invention, that complete sulfonium ion formation of all sulfoxide groups within the polymer may not be accomplished. Typically, the polymer comprises repeating sulfur-containing moieties, about 5–90 percent or more of which have been converted to the corresponding sulfonium ion form, e.g., the ratio of m/n in the formula for the polymeric complex salts is from about 95/5 to about 10/90. Preferably, about 10–50 percent of the sulfur moieties are in the sulfonium ion form.

In view of the number of repeating sulfoxide units in the previously defined polymeric arylsulfoxide, the polymeric triarylsulfonium complex salts of the invention will have total numbers of sulfur-containing moieties, e.g., m+n, of from about 2 to about 30 and preferably from about 2 to about 10.

The complex salt reaction product may be recovered from the reaction mixture by ordinary techniques and purified if desired by repeated washings of water or organic solvents or by recrystallization. The complex salts may be used in some applications, e.g., as corrosion inhibitors, in the crude form. The organosulfonate counterion may easily be converted to other counterions if desired by simple ion-exchange. For example, contacting the complex salts with sodium tetrafluoroborate in, e.g., a methanol solution, will result in preparation of the corresponding tetrafluoroborate salt. Suitable counterions that may be exchanged for the organosulfonates according to this procedure include anionic remnants of strong protonic acids formed by removal of a hydrogen ion from an acid of the formula $HMX_n$ where M is a metal, X is halogen and n is an integer signifying the number of halogens present. Preferred are such counterions as $BF_4^-$, $PF_6^-$, $AsF_6^-$ and $SbF_6^-$, which are useful in initiating the polymerization of cationically polymerizable monomers. Particularly preferred triarylsulfonium salts in this regard are tris-(4-phenoxyphenyl)sulfonium salts of the above counterions.

SPECIFIC EMBODIMENTS

Having described the invention the following examples are provided as further illustration and are not to be construed as limiting.

EXAMPLE 1

A mixture of 10 g (28.2 mmole) of bis-(4-phenylphenyl)sulfoxide, 26 g (282.0 mmole) of toluene and 27.11 g (282.0 mmole) of methane sulfonic acid were refluxed (ca. 110° C.) for 24 hours. The mixture was poured into 300 ml of water plus 300 ml of toluene. The sulfonium salt precipitated as a gummy solid and was purified by decanting the water and toluene, adding further quantities of water to the gummy residue, and stirring. The water was again decanted and the procedure repeated with toluene. The residue was dissolved in 250 ml of chloroform and dried by extracting with saturated aqueous sodium chloride solution followed by treatment with magnesium sulfate. The chloroform was then evaporated and the residue dissolved in methanol. The methanol was then evaporated to leave 9.14 g of sulfonium salt with methanol of solvation. Analysis by nuclear magnetic resonance spectroscopy indicated the residue contained by weight 14.5 percent methanol, 20.5 percent phenyl-bis-(4-phenylphenyl)sulfonium methane sulfonate and 65 percent 4-methylphenyl-bis-(4-phenylphenyl)sulfonium methane sulfonate. This represented a 60.1 percent yield of sulfonium salts.

EXAMPLE 2

A mixture of 192.22 g of methane sulfonic acid, 54.46 g of bis-(4-methoxyphenyl)sulfoxide and 500 ml of anisole was heated at 80° C. for 22 hours. The mixture was poured into 1000 g of ice water and extracted three times with 500-ml portions of ether. The aqueous phase was neutralized with 50 percent aqueous sodium hydroxide and extracted five times with 500-ml portions of chloroform. The combined chloroform phases were dried with magnesium sulfate and the chloroform was removed on a rotary evaporator to give 105.76 g of tris-(4-methoxyphenyl)sulfonium methane sulfonate with residual chloroform of solvation.

EXAMPLE 3

A mixture of 42.51 g of bis-(4-phenoxyphenyl)sulfoxide, 187.23 g of diphenyl ether and 105.71 g of methane sulfonic acid was heated at 100° C. for 24 hours with stirring. The mixture was poured into 700 g of ice water and the resultant aqueous and sulfonium layers extracted four times with 200-ml portions of ether and five times with 200-ml portions of chloroform. The combined chloroform extracts were dried with magnesium sulfate and the chloroform removed on a rotary evaporator to give 91.66 g of tris-(4-phenoxyphenyl)sulfonium methane sulfonate with 1.7 equivalents of chloroform of solvation. This represents a 100 percent yield.

The sulfonium salt was converted in quantitative yield to the corresponding sulfonium tetrafluoroborate salt by treatment with sodium tetrafluoroborate in methanol. The crystalline product was recovered by filtration.

EXAMPLE 4

A mixture of 40.45 g pheny sulfoxide, 340.42 g of diphenyl ether and 192.20 g of methane sulfonic acid was heated at 100° C. for 68 hours. The disappearance of phenyl sulfoxide was monitored by gas chromatography. Workup substantially according to the method of Example 3 gave 49.24 g of diphenyl-4-phenoxyphenylsulfonium methane sulfonate (54.6 percent yield).

EXAMPLE 5

The reaction conditions of Example 4 were substantially repeated by reacting bis-(4-methylphenyl)sulfoxide and diphenyl ether for 24 hours at 80° C. followed by further reaction at 100° C. for 24 hours. Yield of bis-(4-methylphenyl)-4-phenoxyphenylsulfonium methane sulfonate was 71.6 percent.

EXAMPLE 6

A mixture of 3 g of bis-(4-t-butylphenyl)sulfoxide, 30 ml of t-butylbenzene and 9.17 g of methane sulfonic acid was heated at 100° C. for 24 hours. The mixture was poured into 100 ml of water and extracted with four 50-ml portions of ether followed by five 50-ml portions of chloroform. The chloroform extracts were dried and the chloroform removed on a rotary evaporator to give 1.03 g of tris-(4-t-butylphenyl)sulfonium methane sulfonate (20.6 percent yield).

EXAMPLE 7

A mixture of 50.24 g of bis-(4-phenoxyphenyl)sulfoxide, 140.58 g of anisole and 124.93 g of methane sulfonic acid was heated at 100° C. for 24 hours. The mixture was poured into 700 g of ice water and worked up substantially according to the previously described procedure to give 67.6 g of 4-methoxyphenyl-bis-(4-phenoxyphenyl)sulfonium methane sulfonate (91 percent yield).

EXAMPLE 8

A mixture of 30 g of bis-(4-n-butoxyphenyl)sulfoxide, 147.4 g of diphenyl ether and 83.22 g of methane sulfonic acid was heated at 100° C. for 23 hours and worked up substantially according to the previously described procedure to give 49.51 g of a product mixture containing bis-(4-n-butoxyphenyl)-4-phenoxyphenylsulfonium methane sulfonate and dealkylated by-products.

EXAMPLE 9

A mixture of 5.8 g of bis-(4-phenoxyphenyl)sulfoxide and 2.55 g of diphenyl ether in 18 ml of methylene chloride was added dropwise over a period of 3 hours to 7.21 g of methane sulfonic acid at 100° C. The methylene chloride was distilled off as the addition proceeded. The mixture was then heated at 100° C. for 28 hours and worked up substantially according to the procedure previously described to give 7.74 g of tris-(4-phenoxyphenyl)sulfonium methane sulfonate (81.3 percent yield).

EXAMPLE 10

Polymeric Sulfonium Complex Salt

A solution of 17.02 g of diphenyl ether and 11.9 g of thionyl chloride in 100 ml of methylene chloride was added dropwise with stirring over a period of 2 hours to a solution of 14.67 g of aluminum chloride in 15 ml of nitromethane plus 100 ml of methylene chloride at 0° C.–10° C. The mixture was stirred for 2 hours at 25° C. after the addition was complete, then poured into 200 g of ice water. The organic phase was separated and extracted with two 200-ml portions of water and one 100-ml portion of saturated aqueous sodium chloride. The methylene chloride was removed on a rotary evaporator and the residue dissolved in chloroform (100-ml). The chloroform solution was dried with magnesium sulfate and added dropwise to vigorously stirred ether (500-ml). The precipitated polymer was filtered off and vacuum dried to give 18.96 g (87.7 percent yield) of a polymeric arylsulfoxide corresponding to the formula

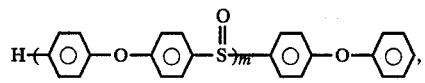

wherein m' was about 10 as determined by end group analysis by $^1$H nuclear magnetic resonance spectroscopy.

A mixture of 15 g of the polymeric sulfoxide prepared above, 118.06 g of diphenyl ether and 66.66 g of methane sulfonic acid was heated at 100° C. for 24 hours. The mixture was worked up substantially according to the previously described process of Example 1 to give a polymer in which 40 percent of the original sulfoxide groups were converted into sulfonium salts as determined by $^1$H nuclear magnetic resonance spectroscopy analysis.

What is claimed is:

1. A process for preparing triarylsulfonium complex salts corresponding to the formula:

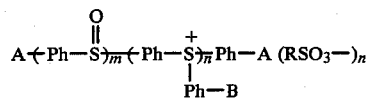

wherein

Ph is phenylene, diphenylene or oxydiphenylene;

A and B independently each occurrence are hydrogen, $C_{1-4}$ alkyl, phenyl, $C_{1-4}$ alkoxy or phenoxy;

R is lower alkyl, phenyl or tolyl;

m is an integer greater than or equal to zero, equal to the number of sulfoxide moieties in the complex salt; and n is an integer greater than or equal to one, equal to the number of sulfonium moieties in the complex salt comprising contacting a diarylsulfoxide or polymeric arylsulfoxide corresponding to the formula

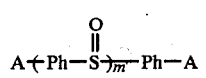

with an aromatic compound of the formula B—Ph—H in the presence of an organosulfonic acid of the formula RSO$_3$H at elevated temperatures wherein A, Ph, B and R are as previously defined; and m' is an integer greater than or equal to one, equal to the number of sulfoxide moieties in the compound.

2. The process of claim 1 which is conducted at a temperature from about 70° C. to about 150° C.

3. The process of claim 2 which is conducted at a temperature from about 80° C. to about 110° C.

4. A process according to claim 1 wherein an excess of organosulfonic acid is present.

5. A process according to claim 4 wherein the organosulfonic acid is present in an amount from about 5 to about 10 equivalents per equivalent of diarylsulfoxide or polymeric arylsulfoxide reactant.

6. A process according to claim 1 wherein from about 1 equivalent to about 10 equivalents of aromatic compound per equivalent of diarylsulfoxide or polymeric arylsulfoxide reactant is present.

7. A process according to claim 1 wherein the organosulfonic acid is methane sulfonic acid, benzene sulfonic acid or toluene sulfonic acid.

8. A process according to claim 1 wherein an inert organic solvent is additionally present.

9. A process according to claim 8 wherein the inert organic solvent is a halogenated aliphatic compound.

10. A process according to claim 1 wherein the diarylsulfoxide or polymeric arylsulfoxide is diphenylsulfoxide, or $C_{1-4}$ alkyl, $C_{1-4}$ alkoxy, or phenoxy-substituted derivatives thereof, or a polymeric arylsulfoxide of the formula

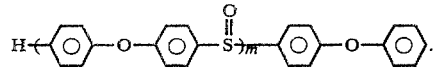

11. A process according to claim 10 wherein m' is from about 2 to about 30.

12. A process according to claim 11 wherein m' is from about 2 to about 10.

13. A process according to claim 10 wherein the diarylsulfoxide is bis(4-phenoxyphenyl)sulfoxide.

14. A process according to claim 1 wherein the aromatic comound is selected from the group consisting of benzene, monosubstituted $C_{1-4}$ alkyl benzenes, monosubstituted $C_{1-4}$ alkoxy benzenes, phenylbenzene and diphenylether.

15. A process according to claim 14 wherein the aromatic compound is toluene, methoxybenzene or diphenylether.

* * * * *